United States Patent
Li

(10) Patent No.: US 10,675,330 B2
(45) Date of Patent: Jun. 9, 2020

(54) INJECTABLE BONE MORPHOGENETIC PROTEIN

(71) Applicant: Warsaw Orthopedic, Inc., Warsaw, IN (US)

(72) Inventor: Ping Li, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 15/927,553

(22) Filed: Mar. 21, 2018

(65) Prior Publication Data

US 2019/0290731 A1 Sep. 26, 2019

(51) Int. Cl.
| | |
|---|---|
| *A61K 38/18* | (2006.01) |
| *A61P 19/08* | (2006.01) |
| *A61K 9/08* | (2006.01) |
| *A61P 19/00* | (2006.01) |
| *A61K 9/00* | (2006.01) |

(52) U.S. Cl.
CPC ........ *A61K 38/1875* (2013.01); *A61K 9/0019* (2013.01); *A61K 9/08* (2013.01); *A61P 19/00* (2018.01); *A61P 19/08* (2018.01)

(58) Field of Classification Search
None
See application file for complete search history.

(56) References Cited

U.S. PATENT DOCUMENTS 5,645,084 A * 7/1997 McKay ................ A61F 2/4455
128/898

FOREIGN PATENT DOCUMENTS

| | | |
|---|---|---|
| CN | 1443571 A | 9/2003 |
| WO | 01-28602 A1 | 4/2001 |
| WO | 0128603 A1 | 4/2001 |

OTHER PUBLICATIONS

Einhorn et al., J. Bone Joint Surg. Am., 2003, vol. 85(8):1425-1435.*
Haralampos Dinopoulos, Peter V. Giannoudis, The use of bone moorphogenetic protiens (BMPs) in long-bone non-unions, Current Orthopaedics, Mini-Symposium: Fracture Healing, Aug. 2007,pp. 268-279, vol. 21, Issue 4.
Saito, N., et al. "Local bone formation by injection of recombinant human bone morphogenetic protein-2 contained in polymer carriers," Bone, 2003, vol. 32, pp. 381-386.
Seo, B. B., et al. "Tuning physical properties and BMP-2 release rates of injectable hydrogel systems for an optimal bone regeneration effect," Biomaterials, 2017, vol. 122, pp. 91-104.
Agrawal, V., et al. "A review on carrier systems for bone morphogenetic protein-2," Journal of Biomedical Materials Research B: Applied Biomaterials. May 2017, vol. 105B, Issue 4, pp. 904-925.
International Search Report and Written Opinion of the International Searching Authority (ISA/KR) dated Jun. 26, 2019 and issued in International Application No. PCT/US2019/022175 filed on Mar. 14, 2019.

* cited by examiner

Primary Examiner — Xiaozhen Xie

(57) ABSTRACT

A method of treating a bone defect is provided. The method comprises administering to the bone defect an injectable solution comprising about 20 µg to about 5000 µg of bone morphogenetic protein-2 (BMP-2) in an aqueous carrier. Kits and methods of making are also provided.

9 Claims, 5 Drawing Sheets

| GROUP | HEALED | NON-HEALED | % HEALED |
|---|---|---|---|
| NON-TREATED CONTROL | 5 | 3 | 63% |
| PBS INJECTION CONTROL | 4 | 4 | 50% |
| rhBMP-2 | 7 | 1 | 88% |

FIG. 3

INJECTABLE BONE MORPHOGENETIC PROTEIN

BACKGROUND

Bone detects may be caused by a number of different factors including, but not limited to, trauma, pathological disease or surgical intervention. Because bone provides both stability and protection to an organism, these detects can be problematic. In order to address these defects, compositions and carriers that contain both natural and synthetic materials have been developed. These compositions and carriers may, depending upon the materials contained within them, be used to repair tissues and to impart desirable biological and/or mechanical properties to the bone defect.

Compositions and carriers may contain materials that are found in mammalian bone tissue which contains one or more proteinaceous materials, active during growth and natural bone healing that can induce a developmental cascade of cellular events resulting in bone formation. Various developmental factors are present in bone. These include bone morphogenetic proteins (BMPs), other bone inductive proteins, bone growth factors, or osteogenic proteins.

BMPs are a class of proteins in the superfamily of transforming growth factor-beta (TGF-β) thought to have osteoinductive or growth-promoting activities on endogenous bone tissue, or function as pro-collagen precursors. Because of these qualities, BMP has been commonly used in conjunction with compositions and carriers (e.g., bone scaffolds and matrices) for bone formation at bone defect sites and bone void sites. For example, bone morphogenetic protein 2 (BMP-2) is commonly placed on a collagen carrier and implanted at a target tissue site. Once the collagen carrier is implanted, it becomes a stationary matrix and the BMP-2 would draw osteoblasts and osteoclasts into the matrix in order to form new bone for fusion. The matrix containing the BMP-2 will promote the migration, proliferation and differentiation of bone cells for bone regeneration.

Generally, it was assumed that BMP-2 required delivery on a stationary matrix in order for it to be effective. It was thought that for the BMP-2 to remain biologically active, a stationary matrix was needed to preserve the conformational integrity of at least a core sequence of the protein's amino acids while at the same time protecting the protein's multiple functional groups from degradation. A matrix was believed to protect unreleased protein from direct contact with bodily fluid which could degrade the protein.

However, in situations where a stationary matrix is not wanted, such as bone defects in a high area of circulation where the matrix can dislodge and form an unwanted thrombosis, an injectable solution would be more desirable. Further, there may be difficulty when injecting a matrix percutaneously into a target bone defect site due to its size, new bone forming solutions are needed. Therefore, new methods and compositions to deliver BMP to a bone defect would be beneficial. Further, new dosing regimens that allow easy administration to a bone defect that avoids the use of a stationary matrix would also be desirable.

SUMMARY

Low dose BMP-2 compositions (e.g., 20 μg to about 5000 μg), methods and kits are provided that allow osteogenesis, osteoinduction and/or osteoconduction without the need for a stationary matrix. In some embodiments, a method of treating a bone defect is provided. The method comprises administering to the bone defect an injectable solution comprising 20 μg to about 5000 μg of bone morphogenetic protein 2 (BMP-2) in an aqueous carrier. The aqueous carrier can comprise saline, dextrose, sterile water for injection, phosphate buffered saline, blood, or a combination thereof. In some embodiments, the injectable solution is administered as a single dose injection to the bone defect, and the BMP-2 is rhBMP-2. In some embodiments, the injectable solution is administered percutaneously to a long bone fracture; the injectable solution is injected directly into a fracture site that has a hematoma; or the aqueous carrier is not osteoinductive or osteoconductive.

In some embodiments, a method of making an injectable bone morphogenetic protein 2 solution is provided. The method comprises mixing 800 μg to about 5000 μg of lyophilized bone morphogenetic protein 2 (BMP-2) with an aqueous carrier to form the injectable bone morphogenetic protein 2 solution. The BMP-2 can be rhBMP-2 and in some embodiments, the aqueous carrier comprises saline, dextrose, sterile water for injection, phosphate buffered saline, blood, or a combination thereof. In some embodiments, the injectable solution further comprises a buffering agent comprising tris(hydroxymethyl)aminomethane (Tris), ethylenediamineetetraacetic acid (EDTA), (2-[4-(2-hydroxyethyl)-1-piperazinyl]ethanesulfonic acid) (HEPES), sodium acetate, sodium citrate, sodium phosphate, 2-(N-morpholino)ethanesulfonic acid (MES), phosphate buffered saline (PBS), sodium phosphate, potassium phosphate, sodium chloride, potassium chloride, glycerol, calcium chloride, sucrose, glycine, L-glutamic acid, polysorbate. polysorbate 80 or a combination thereof. In some embodiments, the buffering agent comprises sucrose, glycine, L-glutamic acid, sodium chloride, polysorbate 80 or a combination thereof; the buffering agent is in the injectable solution at a concentration from about 1 mM to 100 mM; or the injectable solution has a pH of from about 4.0 to about 6.0.

In some embodiments, a kit for treating a bone defect is provided. The kit comprises a 20 μg to about 5000 μg dosage of injectable bone morphogenetic protein 2 (BMP-2); an aqueous carrier to mix the injectable BMP-2; and a set of instructions for administering the injectable BMP-2. In some embodiments, the injectable BMP-2 is in lyophilized form; or the kit comprises a plurality of doses of injectable BMP-2; or the kit further comprises a pump for administering the 800 μg to about 5000 μg dosage of injectable BMP-2. In some embodiments, the aqueous carrier comprises a buffering agent.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings.

FIG. 3 is a table of the results of the experiment of FIG. 2. The results of the administration of the non-treated control showed healing in five of the rats, while three of the rats did not heal, and the percentage of healing was 63%. The results of the administration of the PBS injection control showed healing in four of the rats, while four of the rats did not heal, and the percentage of healing was 50%. The results of the administration of the single injection of low-dose rhBMP-2 without a matrix showed healing in seven of the rats, while 1 of the rats did not heal and the percentage of healing was 88%.

Figure 1:
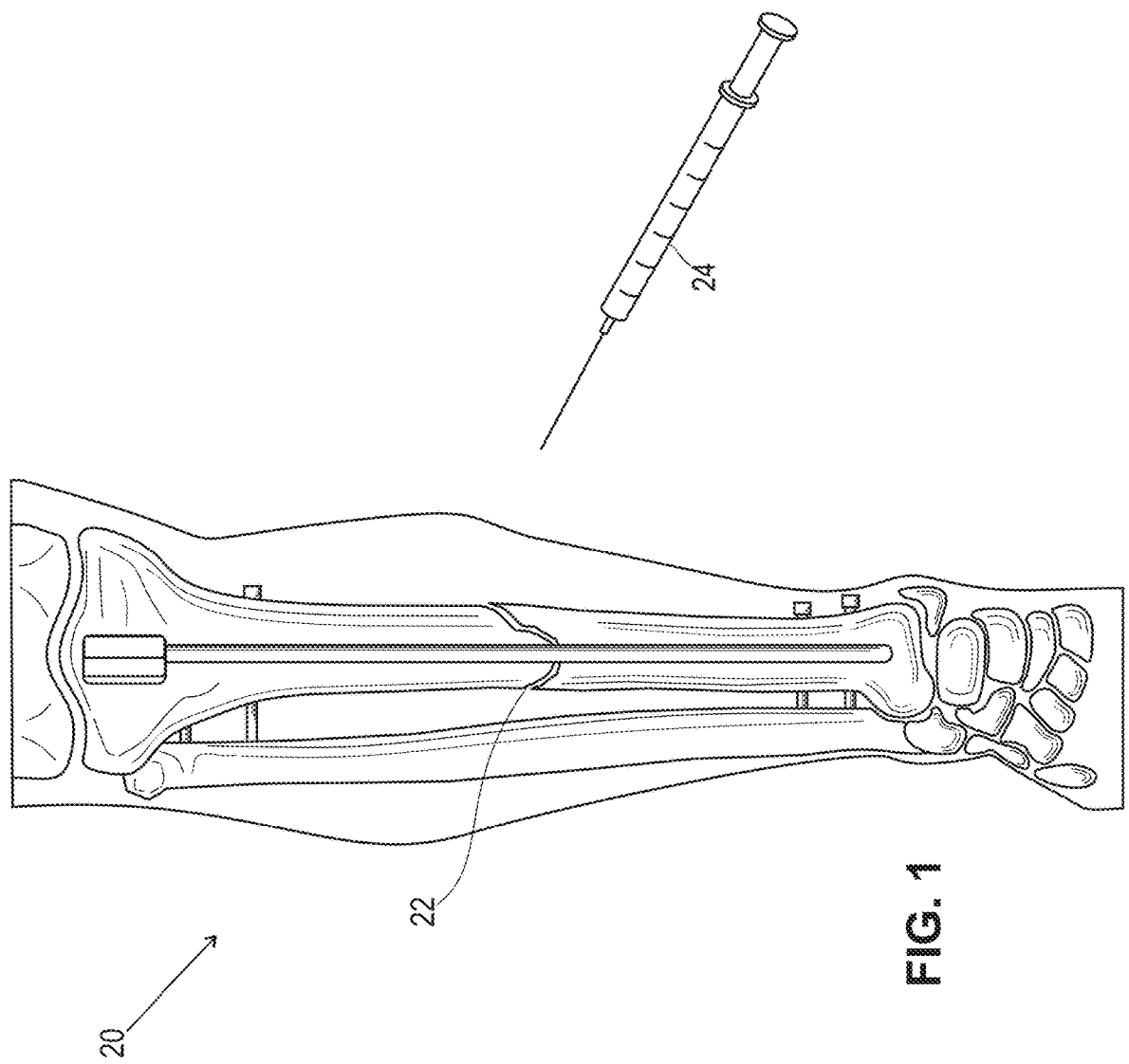
FIG. 1 is an illustration of one embodiment of an injectable bone morphogenetic protein-2 solution disposed in a syringe that is being administered to a bone defect site. The bone defect site can be a long bone fracture as shown and the injectable bone morphogenetic protein-2 solution is administered to the bone defect site percutaneously.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of promoting an understanding of the principles of the disclosure, reference will now be made to certain embodiments and specific language will be used to describe the same. It will nevertheless be understood that no limitation of the scope of the disclosure is thereby intended, such alterations and further modifications in the illustrated device, and such further applications of the principles of the disclosure as described herein being contemplated as would normally occur to one skilled in the art to which the disclosure relates.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical representations are as precise as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Additionally, unless defined otherwise or apparent from context, all technical and scientific terms used herein have the same meanings as commonly understood by one of ordinary skill in the art to which this disclosure belongs.

Unless explicitly stated or apparent from context, the following terms are phrases have the definitions provided below:

DEFINITIONS

It is noted that, as used in this specification and the appended claims, the singular forms "a," "an," and "the," include plural referents unless expressly and unequivocally limited to one referent. Thus, for example, reference to "a dose" includes one, two, three or more doses.

The term "patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

The term "mammal" refers to organisms from the taxonomy class "mammalian," including but not limited to humans, other primates such as chimpanzees, apes, orangutans and monkeys, rats, mice, cats, dogs, cows, horses, etc.

A "therapeutically effective amount" or "effective amount" is such that when administered, the drug (e.g., growth factor) results in alteration of the biological activity, such as, for example, promotion of bone, cartilage and/or other tissue (e.g., vascular tissue) growth, reduction or alleviation of pain, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired.

The terms "treating" and "treatment" when used in connection with a disease or condition refer to executing a protocol that may include a bone repair procedure, where the bone implant and/or one or more drugs are administered to a patient (human, other normal or otherwise or other mammal), in an effort to alleviate signs or symptoms of the disease or condition or immunological response. Alleviation can occur prior to signs or symptoms of the disease or condition appearing, as well as after their appearance. Thus, treating or treatment includes preventing or prevention of disease or undesirable condition. In addition, treating, treatment, preventing or prevention do not require complete alleviation of signs or symptoms, does not require a cure, and specifically includes protocols that have only a marginal effect on the patient.

The term "bone," as used herein, refers to bone that is cortical, cancellous or cortico-cancellous of autogenous, allogeneic, xenogeneic, or transgenic origin.

The term "osteoconductive," as used herein, refers to the ability of a non-osteoinductive substance to serve as a suitable template or substance along which bone may grow.

The term "osteoinductive," as used herein, refers to the quality of being able to recruit cells from the host that have the potential to stimulate new bone formation. Any material that can induce the formation of ectopic bone in the soft tissue of an animal is considered osteoinductive. In some embodiments, the osteoinductive material comprises BMP-2. Osteoinduction refers to the ability to stimulate the proliferation and differentiation of pluripotent mesenchymal stem cells (MSCs). In endochondral bone formation, stem cells differentiate into chondroblasts and chondrocytes, laying down a cartilaginous ECM, which subsequently calcifies and is remodeled into lamellar bone. In intramembranous bone formation, the stem cells differentiate directly into osteoblasts, which form bone through direct mechanisms. Osteoinduction can be stimulated by osteogenic growth factors, although some ECM proteins can also drive progenitor cells toward the osteogenic phenotype.

The term "parenteral," as used herein, refers to modes of administration which bypass the gastrointestinal tract, and include for example, intramuscular, intraperitoneal, intrasternal, subcutaneous, percutaneously, intra-operatively, intrathecally, intradiskally, peridiskally, epidurally, perispinally, intraarticular or combinations thereof.

The term "osteoconduction" refers to the ability to stimulate the attachment, migration, and distribution of vascular and osteogenic cells within a matrix. The physical characteristics that affect the matrix's osteoconductive activity include porosity, pore size, and three-dimensional architecture. In addition, direct biochemical interactions between matrix proteins and cell surface receptors play a major role in the host's response to the matrix.

The term "osteogenic" refers to the ability of the injectable solution to produce bone independently. To have direct osteogenic activity, the injectable solution must contain cellular components that directly induce bone formation. For example, an allograft seeded with activated MSCs would have the potential to induce bone formation directly, without recruitment and activation of host MSC populations. Because many osteoconductive allografts also have the ability to bind and deliver bioactive molecules, their osteoinductive potential will be greatly enhanced.

"Resorbable", as used herein, refers to a matrix that exhibits chemical dissolution when placed in a mammalian body. The injectable bone morphogenetic protein does not need a stationary resorbable matrix. For example, the stationary matrix comprises an implant that is fixed in the body at the bone defect for a period of time. The matrix can be resorbable and/or non-resorbable for that period of time (e.g., 3 days to 6 months).

The term "solution" refers to a homogeneous liquid preparation that contains one or more chemical substances dissolved (e.g., molecularly dispersed), in a suitable solvent or mixture of mutually miscible solvents. Typically, solutions are mixtures with particle sizes of less than $10^{-7}$ cm. The aqueous carrier that is used to administer the BMP can be a solution.

The term "suspension" refers to a two-phase system with uniform dispersion of finely divided solid particles in a continuous phase of liquid in which the particles have minimum solubility and a particle size greater than $10^{-5}$ cm. Here in suspensions, the finely divided solid particles are called as dispersed phase or external phase or discontinuous phase and the phase in which they are dispersed is called as dispersion medium or internal phase or continuous phase. The aqueous carrier that is used to administer the BMP can be a suspension.

Reference will now be made in detail to certain embodiments of the disclosure. The disclosure is intended to cover all alternatives, modifications, and equivalents that may be included within the disclosure as defined by the appended claims.

The headings below are not meant to limit the disclosure in any way; embodiments under any one heading may be used in conjunction with embodiments under any other heading.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

Injectable Bone Morphogenetic Protein

A method of treating a bone defect with BMP-2 is shown in 20, where a solution of BMP-2 is provided that is administered to a patient in order to create bone growth at the site of an injury such as a bone defect 22, as shown in FIG. 1. Illustrative target tissue sites (e.g., bone defect sites) that can be treated with injectable solution of the disclosure include, for instance, those resulting from injury, defects brought about during the course of surgery, infection, malignancy or developmental malformation. Specific bones which can be repaired or replaced with the bone material include, but are not limited to the ethmoid; frontal; nasal; occipital; parietal; temporal; mandible; maxilla; zygomatic; cervical vertebra; thoracic vertebra; lumbar vertebra; sacrum; rib; sternum; clavicle; scapula; humerus; radius; ulna; carpal bones; metacarpal bones; phalanges; ilium; ischium; pubis; femur; tibia; fibula; patella; calcaneus; tarsal and metatarsal bones. In some embodiments, the injectable solution is administered percutaneously to a long bone fracture.

The injectable solution comprises a therapeutically effective amount of BMP, such as BMP-2 in an amount of about 20 μg to about 5000 μg in an aqueous carrier. In some embodiments, the BMP-2 is rhBMP-2. The BMP-2 can be administered at low dose, such as, in an amount of about 840 μg to about 4500 μg, about 1000 μg to about 4000 μg, about 1500 μg to about 3500 μg, about 2000 μg to about 3000 μg, or about 2500 μg to about 2750 μg to fuse the bone defect. In some embodiments, the amount of BMP-2 administered is from about 20, 50, 75, 100, 125, 150, 175, 200, 225, 250, 275, 300, 325, 350, 375, 400, 425, 450, 500, 525, 550, 575, 600, 625, 650, 675, 700, 725, 750, 775, 800, 825, to about 850 μg.

In some embodiments, the amount of BMP-2 administered is from about 840, 850, 860, 870, 880, 890, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900 to about 5000 μg.

The BMP can be in an amount of about 1 to about 98% of the injectable solution. In some embodiments, the BMP is in an amount of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 to about 99% of the injectable solution.

The BMP may include, but is not limited to, BMP-1, BMP-2, BMP-3, BMP-4, BMP-5, BMP-6, BMP-7, BMP-8, BMP-9, BMP-10, BMP-12, BMP-13, BMP-15, BMP-16, BMP-17, BMP-18, as well as polynucleotides or polypeptides thereof, as well as any combination of one or more of these BMPs, including full length BMPs or fragments thereof, or combinations thereof, either as polypeptides or polynucleotides encoding the polypeptide fragments of all of the recited BMPs.

As described above, the injectable solution comprises an aqueous carrier. The aqueous carrier is not osteoinductive or osteoconductive and is only used as a vehicle for delivery of the selected type or types of BMP. The aqueous carrier can include, but is not limited to, saline, dextrose, sterile water for injection, phosphate buffered saline, blood, or a combination thereof. The aqueous carrier can be blood, for example, the patient's own blood and the blood can be combined with clotting factors.

Exemplary aqueous carriers include, but are not limited to, sterile water, bacteriostatic water for injection (BWFI), a pH buffered solution (e.g. phosphate-buffered saline), sterile saline solution, Ringer's solution or dextrose solution.

The aqueous carrier can be in an amount of about 1, 2, 3, 4, 5, 6, 7, 8, 9 or 10 ml. For example, the injectable solution can comprise 20 µg of BMP-2 or rh-BMP-2 in 1 ml of an aqueous carrier, 40 µg of BMP-2 or rh-BMP-2 in 2 ml of an aqueous carrier, 60 µg of BMP-2 or rh-BMP-2 in 3 ml of an aqueous carrier, 80 µg of BMP-2 or rh-BMP-2 in 1 ml of an aqueous carrier, 100 µg of BMP-2 or rh-BMP-2 in 2 ml of an aqueous carrier, 120 µg of BMP-2 or rh-BMP-2 in 3 ml of an aqueous carrier, 140 µg of BMP-2 or rh-BMP-2 in 1 ml of an aqueous carrier, 160 µg of BMP-2 or rh-BMP-2 in 2 ml of an aqueous carrier, or 180 µg of BMP-2 or rh-BMP-2 in 2 ml of an aqueous carrier or 200 µg of BMP-2 or rh-BMP-2 in 2 ml of an aqueous carrier.

In some embodiments, the injectable solution can comprise 840 µg of BMP-2 or rh-BMP-2 in 1 ml of an aqueous carrier, 840 µg of BMP-2 or rh-BMP-2 in 2 ml of an aqueous carrier, 840 µg of BMP-2 or rh-BMP-2 in 3 ml of an aqueous carrier, 1600 µg of BMP-2 or rh-BMP-2 in 1 ml of an aqueous carrier, 1600 µg of BMP-2 or rh-BMP-2 in 2 ml of an aqueous carrier, 1600 µg of BMP-2 or rh-BMP-2 in 3 ml of an aqueous carrier, 2400 µg of BMP-2 or rh-BMP-2 in 1 ml of an aqueous carrier, 2400 µg of BMP-2 or rh-BMP-2 in 2 ml of an aqueous carrier, 2400 µg of BMP-2 or rh-BMP-2 in 3 ml of an aqueous carrier, 3200 µg of BMP-2 or rh-BMP-2 in 1 ml of an aqueous carrier, 3200 µg of BMP-2 or rh-BMP-2 in 2 ml of an aqueous carrier, 3200 µg of BMP-2 or rh-BMP-2 in 3 ml of an aqueous carrier, 4500 µg of BMP-2 or rh-BMP-2 in 1 ml of an aqueous carrier, 4500 µg of BMP-2 or rh-BMP-2 in 2 ml of an aqueous carrier, or 4500 µg of BMP-2 or rh-BMP-2 in 3 ml of an aqueous carrier.

The aqueous carrier can be in an amount of about 1 to about 99.9% of the injectable solution. In some embodiments, the aqueous carrier is in an amount of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 87, 88, 89, 90, 91, 92, 93, 94, 95, 96, 97 to about 99.9% of the injectable solution.

The injectable solution can comprise a buffering agent, including, but not limited to, tris(hydroxymethyl)aminomethane (Tris), ethylenediaminetetraacetic acid (EDTA), (2-[4-(2-hydroxyethyl)-1-piperazinyl]ethanesulfonic acid) (HEPES), sodium acetate, sodium citrate, sodium phosphate, 2-(N-morpholino)ethanesulfonic acid (MES), phosphate buffered saline (PBS), sodium phosphate, potassium phosphate, sodium chloride, potassium chloride, glycerol, calcium chloride, sucrose, glycine, L-glutamic acid, polysorbate 80 or a combination thereof. In some embodiments, the buffering agent is sucrose, glycine, L-glutamic acid, sodium chloride, polysorbate 80 or a combination thereof.

Additional buffering agents may include, but are not limited to, alkaline earth metal carbonates, phosphates, bicarbonates, citrates, borates, acetates, succinates, or others. Illustrative-specific buffering agents include for instance sodium phosphate, sodium citrate, sodium borate, sodium acetate, sodium bicarbonate, and sodium carbonate.

The buffering agent can be in the injectable solution at a concentration from about 1 mM to 100 mM. The buffering agent can be in the injectable solution at a concentration of from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to about 100 mM.

The injectable solution can have a pH of from about 4.0 to about 6.0. It is contemplated that the pH of the injectable solution can be from about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9 to about 6.0.

The injectable solution can be administered as a single dose injection to the bone defect. The bone defect can include those described above and, in some embodiments, the bone defect is a long bone fracture and the injectable solution is administered percutaneously to the long bone fracture. The injectable solution can also be administered in multiple injection doses to the bone defect such as 1, 2, 3, 4, 5, 6, 7, 8, 9 or 10 injections per day, per week or per month depending on the severity of the defect and/or response to treatment.

The injectable solution can be administered via a syringe 24, as shown in FIG. 1. The syringe can have variously sized cannulas/needles and in some embodiments, the cannulas/needles can have a size of from about 16 gauge to about 30 gauge, from about 20 to about 28 gauge, or from about 22 to about 26 gauge. The size of the cannulas/needles can be from about 16, 17, 18, 19, 20, 21, 22, 23, 24, 25, 26, 27, 28, 29 or 30 gauge. The syringe can be configured to be administered to the bone defect based on its location (e.g., leg, hip, spine, knee, etc.) Another way the injectable solution can be administered is through a pump, as described below with regard to the methods of treatment. A pump and/or multiple syringes can also be used to administer multiple injection doses of the injectable solution.

In some embodiments, the injectable solution is injected directly into a fracture site that has a hematoma. The injectable solution can be administered in multiple intermittent bolus injections at different stages of healing of a bone fracture. For example, a first intermittent bolus injection is administered at a time of injury during a hematoma formation, a second intermittent bolus injection is administered between one to about two weeks at an onset of a bone reparative phase, and a third intermittent bolus injection is administered at an onset of a bone remodeling phase.

Multiple injections of the injectable solution can be administered to a target tissue site (e.g., bone defect) over a period of time. For example, weekly injections of the injectable solution in an amount of about 1, 2, 3, 4, 5 or 6 injections directly into a bone defect (e.g., long bone fracture site) can be administered to a patient for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 up to 52 weeks.

The injectable solution of the present disclosure is an effective bone growth product and assists in the healing process at a site of a target tissue site (e.g., bone defect such as a long bone fracture). In particular, the BMP in the injectable solution is osteoinductive and osteoconductive and facilitates bone growth at the target tissue site.

Additives

The injectable solution can further comprise additives such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfate, sodium bisulfite, sodium thiosulfate, thimerosal, methylparaben, polyvinyl alcohol and phenylethyl alcohol; solubility adjusting agents; stabilizers; and/or cohesion modifiers. In some embodiments, the injectable solution may comprise sterile and/or preservative free material. These additives may have multi-functional purposes including the carrying and stabilizing of the BMP. The additives as described above, can be in an amount of about 0.001 to about 5 wt. % of the injectable solution. The additives can be in an amount of about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 1, 2, 3, 4 or 5% of the injectable solution.

The injectable solution can include clotting factors, including, but not limited to fibrinogen, prothrombin, tissue thromboplastin (tissue factor), ionized calcium (Ca++), labile factor or proaccelerin, stable factor or proconvertin, antihemophilic factor, plasma thromboplastin component, Christmas factor, Stuart-Prower factor, plasma thromboplastin antecedent, Hageman factor or fibrin-stabilizing factor. The clotting factors may be added to the injectable composition in an amount of about 0.0001% to about 5% of the injectable solution. The clotting factor or factors can be in an amount of about 0.0001, 0.0002, 0.0003, 0.0004, 0.0005, 0.0006, 0.0007, 0.0008, 0.0009, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 1, 2, 3, 4 or 5% of the injectable solution.

In some embodiments, the injectable solution is free from a matrix material particularly a stationary matrix material. The term "free from a matrix," as used herein, refers to the injectable solution of the present disclosure not being disposed in a solid matrix or semi-solid matrix. Thus, injectable BMP is more than 95% to 99.9% to 100% free from matrices including, but not limited to, hydroxyethyl cellulose, hydroxypropyl cellulose, hydroxyethylmethyl cellulose, hydroxypropylmethyl cellulose, poly (alpha-hydroxy acids), poly (lactide-co-glycolide) (PLGA or PLG), polylactide (PLA), polyglycolide (PG), conjugates of poly (alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, caprolactone, dextrans, vinylpyrrolidone, PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, or combinations thereof.

In some embodiments, the injectable solution is a colorless solution and a coloring agent can be added to the colorless solution so that the user can now see the injectable solution's application to the target tissue site. In some embodiments, the mixture of the injectable solution and coloring agent is injected into the target tissue site and then the user can view its distribution within the target tissue site.

The injectable solution may have a molecular weight of from about 500 to about 30,000 Daltons (Da). In various embodiments, the injectable solution may have a molecular weight of from about 1,000 to about 10,000 Da. In some embodiments, the injectable solution may have a molecular weight of from about 2,000 to 4,000 Da or from about 3,000 to 4,000 Da. In some embodiments, the injectable solution may have a molecular weight of 500, 600, 700, 800, 900, 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000 or about 30,000 Da.

In some embodiments, injectable solution may or may not also contain other beneficial substances including for example preservatives, cosolvents, suspending agents, viscosity enhancing agents, ionic strength and osmolality adjusters and/or other excipients.

One or more additional biologically active ingredients may or may not be added to the resulting injectable solution. These active ingredients may or may not be related to the bone repair capabilities of the injectable solution. Suitable active ingredients are hemostatic agents, genes, growth differentiation factors (GDFs), or other non-collagenic proteins such as PDGF, ostropontin, osteonectin, cytokines, and the like.

In another embodiment, one or more Growth Differentiation Factors ("GDFs") may or may not be added either into the injectable solution or administered to the bone defect site before administration of the injectable solution. Known GDFs include, but are not limited to, GDF-1, GDF-2, GDF-3, GDF-7, GDF-10, GDF-11, and GDF-15. For example, GDFs useful as isolated osteoinductive agents include, but are not limited to, the following GDFs: GDF-1 polynucleotides or polypeptides corresponding to GenBank Accession Numbers M62302, AAA58501, and AAB94786, as well as mature GDF-1 polypeptides or polynucleotides encoding the same. GDF-2 polynucleotides or polypeptides corresponding to GenBank Accession Numbers BC069643, BC074921, Q9UK05, AAH69643, or AAH741921, as well as mature GDF-2 polypeptides or polynucleotides encoding the same. GDF-3 polynucleotides or polypeptides corresponding to GenBank Accession Numbers AF263538, BCO30959, AAF91389, AAQ89234, or Q9NR23, as well as mature GDF-3 polypeptides or polynucleotides encoding the same. GDF-7 polynucleotides or polypeptides corresponding to GenBank Accession Numbers AB158468, AF522369, AAP97720, or Q7Z4P5, as well as mature GDF-7 polypeptides or polynucleotides encoding the same. GDF-10 polynucleotides or polypeptides corresponding to GenBank Accession Numbers BC028237 or AAH28237, as well as mature GDF-10 polypeptides or polynucleotides encoding the same.

GDF-11 polynucleotides or polypeptides corresponding to GenBank Accession Numbers AF100907, NP005802 or O95390, as well as mature GDF-11 polypeptides or polynucleotides encoding the same. GDF-15 polynucleotides or polypeptides corresponding to GenBank Accession Numbers BC008962, BC000529, AAH00529, or NP004855, as well as mature GDF-15 polypeptides or polynucleotides encoding the same.

In some embodiments, the injectable solution contains other bioactive agents or these bioactive agents can be administered to the target tissue site prior to the injectable solution being administered. In certain embodiments, the bioactive agent is a drug. These bioactive agents may include, for example, antimicrobials, antibiotics, antimyobacterial, antifungals, antivirals, antineoplastic agents, antitumor agents, agents affecting the immune response, blood calcium regulators, agents useful in glucose regulation, anticoagulants, antithrombotics, antihyperlipidemic agents, cardiac drugs, thyromimetic and antithyroid drugs, adrenergics, antihypertensive agents, cholinergic, anticholinergics, antispasmodics, antiulcer agents, skeletal and smooth muscle relaxants, prostaglandins, general inhibitors of the allergic response, antihistamines, local anesthetics, analgesics, narcotic antagonists, antitussives, sedative-hypnotic agents, anticonvulsants, antipsychotics, anti-anxiety agents, antidepressant agents, anorexigenics, non-steroidal anti-inflammatory agents, steroidal anti-inflammatory agents, antioxidants, vaso-active agents, bone-active agents, osteogenic factors, antiarthritics, and diagnostic agents.

A more complete listing of bioactive agents and specific drugs suitable for use in the present disclosure may be found in "The Merck Index: An Encyclopedia of Chemicals, Drugs, and Biologicals," Edited by Susan Budavari, et al.; and the United States Pharmacopoeia/National Formulary XXXVII/XXXII, published by the United States Pharmacopeial Convention, Inc., Rockville, Md., 2013, each of which is incorporated herein by reference.

Bioactive agents may also be provided by incorporation into the injectable solution or can be administered before or after the injectable solution is administered. Bioactive agents such as those described herein can be incorporated homogeneously into the injectable solution by simple admixture or otherwise. Further, they may be incorporated alone or in conjunction with another carrier form or medium such as microspheres or another microparticulate formulation. Suitable techniques for forming microparticles are well known in the art, and can be used to entrain or encapsulate bioactive agents, whereafter the microparticles can be dispersed within the bone material upon or after its preparation.

It will be appreciated that the amount of additive used will vary depending upon the type of additive, the specific activity of the particular additive preparation employed, and the intended use of the injectable solution. The desired amount is readily determinable by the user.

Any of a variety of medically and/or surgically useful substances can be incorporated in, or associated with, the injectable solution either before, during, or after preparation of the injectable solution.

Lyophilization

In some embodiments, the BMP is freeze-dried or is in a lyophilized form. Typically, in the freeze-dried or lyophilized form, an effective amount (e.g., 20 μg to about 5000 μg) of the BMP is provided. Lyophilized forms can be reconstituted into solutions, suspensions, emulsions, or any other suitable form for administration or use. Lyophilized BMP is typically first prepared as liquids, then frozen and lyophilized. The total liquid volume before lyophilization can be less, equal to, or more than, the final reconstituted volume of the lyophilized BMP. The lyophilization process is well known to those of ordinary skill in the art, and typically includes sublimation of water from a frozen formulation under controlled conditions.

Lyophilized formulations can be stored at a wide range of temperatures. Lyophilized BMP may be stored at or below 30° C., for example, refrigerated at 4° C., or at room temperature (e.g., approximately 25° C.).

Lyophilized BMP are typically reconstituted for use by addition of an aqueous solution to dissolve the lyophilized BMP. A wide variety of aqueous solutions can be used to reconstitute lyophilized BMP. In some embodiments, lyophilized BMP are reconstituted using water. In some embodiments, lyophilized BMP can be reconstituted with a solution containing water (e.g., USP WFI, or water for injection) or bacteriostatic water (e.g., USP WFI with 0.9% benzyl alcohol). However, solutions comprising buffers and/or excipients and/or one or more pharmaceutically acceptable carriers can also be used. In some embodiments, the solutions do not contain any preservatives (e.g., are preservative free).

In some embodiments, the lyophilized BMP can be disposed in a vial by the manufacturer and then the surgeon can mix the aqueous carrier with the lyophilized BMP and/or with a diluent. This mixture can then be parenterally administered to the target tissue site. Aqueous carriers include, but are not limited to water, e.g., sterile water, solutions containing inorganic salts, or cationic surface active agents including sodium chloride, saline, e.g., phosphate buffered saline, potassium chloride, sodium sulfate, potassium sulfate, EDTA, ammonium sulfate, ammonium acetate, and sodium acetate. Mixtures of two or more aqueous carriers can be used. The aqueous carriers can further include, for example, bone marrow aspirate, platelet concentrate, blood, pharmaceutical additives in solution, or combinations of these materials. Exemplary aqueous carriers include, but are not limited to, sterile water, bacteriostatic water for injection (BWFI), a pH buffered solution (e.g. phosphate-buffered saline), sterile saline solution, Ringer's solution or dextrose solution. These can be used to reconstitute the BMP and dilute it for administration to the patient.

Methods of Treatment

As described above, illustrative target tissue sites (e.g., bone repair or bone defect sites) that can be treated with injectable solution of the disclosure include, for instance, those resulting from injury, defects brought about during the course of surgery, infection, malignancy or developmental malformation. The injectable solution can be used in a wide variety of orthopedic, periodontal, neurosurgical and oral and maxillofacial surgical procedures including, but not limited to the repair of simple and compound fractures and non-unions; external and internal fixations; joint reconstructions such as arthrodesis; general arthroplasty; cup arthroplasty of the hip; femoral and humeral head replacement; femoral head surface replacement and total joint replacement; repairs of the vertebral column including spinal fusion and internal fixation; tumor surgery, e.g., deficit filing; discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay osteoimplants; implant placement and revision; sinus lifts; cosmetic enhancement; etc. Specific bones which can be repaired or replaced with the bone material include, but are not limited to the ethmoid; frontal; nasal; occipital; parietal; temporal; mandible; maxilla; zygomatic; cervical vertebra; thoracic vertebra; lumbar vertebra; sacrum; rib; sternum; clavicle; scapula; humerus; radius; ulna; carpal bones; metacarpal bones; phalanges; ilium; ischium; pubis; femur; tibia; fibula; patella; calcaneus; tarsal and metatarsal bones.

In accordance with certain aspects of the disclosure, the injectable solution of the disclosure can be used in, on or around load bearing implants such as spinal implants, hip implants (e.g. in or around implant stems and/or behind acetabular cups), knee implants (e.g. in or around stems). In some embodiments, the injectable solution of the disclosure can be incorporated in, on or around a load-bearing spinal implant device having a compressive strength of at least about 10000 N, such as a fusion cage, PEEK implants, dowel, or other device potentially having a pocket, chamber or other cavity for containing an osteoinductive composition, and used in a spinal fusion such as an interbody fusion. One illustrative such use is in conjunction with a load-bearing interbody spinal spacer to achieve interbody fusion. In these applications, the injectable solution can be placed in and/or around the spacer to facilitate the fusion.

In some embodiments, a method of treating a bone defect is provided, the method comprising administering to the bone defect an injectable solution comprising 20 μg to about 5000 μg of bone morphogenetic protein-2 (BMP-2) in an aqueous carrier. In some embodiments, the BMP-2 is rhBMP-2. The BMP-2 can be administered in an amount of about 840 μg to about 4500 μg to fuse the bone defect. In some embodiments, the amount of BMP-2 administered is from about 20, 50, 75, 100, 125, 150, 175, 200, 225, 250, 275, 300, 325, 350, 375, 400, 425, 450, 500, 525, 550, 575, 600, 625, 650, 675, 700, 725, 750, 775, 800, 825, to about 850 μg.

In some embodiments, the amount of BMP-2 administered is from about 860, 870, 880, 890, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900 to about 5000 μg. The BMP can be BMP-2 or rhBMP-2, and can also include additional forms of BMP, as described above. The BMP can also be lyophilized BMP, as described herein.

In some embodiments, as described above, the aqueous carrier is not osteoinductive or osteoconductive. Instead, the aqueous carrier can comprise saline, dextrose, sterile water for injection, phosphate buffered saline, blood, or a combination thereof. The aqueous carrier can be blood, for example, the patient's own blood and the blood can be combined with clotting factors.

The injectable solution can further comprise a buffering agent comprising tris(hydroxymethyl)aminomethane (Tris), ethylenediaminetetraacetic acid (EDTA), (2-[4-(2-hydroxyethyl)-1-piperazinyl]ethanesulfonic acid) (HEPES), sodium acetate, sodium citrate, sodium phosphate, 2-(N-morpholino)ethanesulfonic acid (MES), phosphate buffered saline (PBS), sodium phosphate, potassium phosphate, sodium chloride, potassium chloride, glycerol, calcium chloride, sucrose, glycine, L-glutamic acid, polysorbate 80 or a combination thereof. In some embodiments, the buffering agent comprises sucrose, glycine, L-glutamic acid, sodium chloride, polysorbate 80 or a combination thereof.

The buffering agent is in the injectable solution at a concentration from about 1 mM to 100 mM. The buffering agent can be in the injectable solution at a concentration of from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 79, 80, 81, 82, 83, 84, 85, 86, 87, 88, 89, 90, 91, 92, 93, 94, 95, 96, 97, 98, 99 to about 100 mM.

The injectable solution of the method described above has a pH of from about 4.0 to about 6.0. It is contemplated that the pH of the injectable solution can be from about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9 to about 6.0.

In some embodiments, the injectable solution can be administered as a single dose injection to the bone defect. The bone defect can include those described above and, in some embodiments, the bone defect is a long bone fracture and the injectable solution is administered percutaneously to the long bone fracture. The injectable solution can be administered in multiple injection doses to the bone defect such as 1, 2, 3, 4, 5, 6, 7, 8, 9 or 10 injections. For example, the BMP solution can be administered IV over a period of 5 minutes to 1 hour by an IV continuous solution or by a syringe locally at the bone defect or systemically.

One way that the injectable solution can be administered in multiple injection doses is via an implantable pump. Pump parenteral administration may include, for example, an infusion pump that administers the injectable solution through a catheter at or near the bone defect or an implantable mini-pump that can be inserted at or near the bone defect, an implantable controlled release device or sustained release delivery system that can release a certain amount of the injectable solution per hour or in intermittent bolus doses. One example of a suitable pump for use is the SynchroMed® (Medtronic, Minneapolis, Minn.) pump. This pump has three sealed chambers. One contains an electronic module and battery. The second contains a peristaltic pump and drug or solution reservoir. The third contains an inert gas that provides the pressure needed to force the injectable solution into the peristaltic pump. To fill the pump, the injectable solution is injected through the reservoir fill port to the expandable reservoir. The inert gas creates pressure on the reservoir, and the pressure forces the injectable solution through a filter and into the pump chamber. The injectable solution is then pumped out of the device from the pump chamber and into the catheter, which will direct it for deposit at the target site. The rate of delivery of injectable solution is controlled by a microprocessor. This allows the pump to be used to deliver similar or different amounts of injectable solution continuously, continually, at specific times, or at set intervals between deliveries.

In some embodiments, the injectable solution is injected directly into a fracture site that has a hematoma. In some embodiments, the injectable solution is administered in multiple intermittent bolus injections at different stages of healing of a bone fracture. For example, a first intermittent bolus injection is administered at a time of injury during a hematoma formation, a second intermittent bolus injection is administered between one to about two weeks at an onset of a bone reparative phase, and a third intermittent bolus injection is administered at an onset of a bone remodeling phase.

In some embodiments, a method of making an injectable bone morphogenetic protein 2 solution is provided. The method comprises: mixing 20 µg to about 5000 µg of lyophilized bone morphogenetic protein-2 (BMP-2) with an aqueous carrier to form the injectable bone morphogenetic protein-2 solution. In some embodiments, the BMP-2 is rhBMP-2. The aqueous carrier can comprise saline, dextrose, sterile water for injection, phosphate buffered saline, blood, or a combination thereof.

The injectable solution further comprises a buffeting agent comprising tris(hydroxymethyl)aminomethane (Tris), ethylenediaminetetraacetic acid (EDTA), (2-[4-(2-hydroxyethyl)-1-piperazinyl]ethanesulfonic acid) (HEPES), sodium acetate, sodium citrate, sodium phosphate, 2-(N-morpholino)ethanesulfonic acid (MES), phosphate buffered saline (PBS), sodium phosphate, potassium phosphate, sodium chloride, potassium chloride, glycerol, calcium chloride, sucrose, glycine, L-glutamic acid, polysorbate 80 or a combination thereof. In some embodiments, the buffering agent comprises sucrose, glycine, L-glutamic acid, sodium chloride, polysorbate 80 or a combination thereof, the buffering agent is in the injectable solution at a concentration from about 1 mM to 100 mM, as described above; or the injectable solution has a pH of from about 4.0 to about 6.0.

Kits

The present application also provides a kit for treating a bone defect, the kit comprising an 20 µg to about 5000 µg dosage of injectable bone morphogenetic protein-2 (BMP-2); an aqueous carrier to mix the injectable BMP-2; and a set of instructions for administering the injectable BMP-2.

In some embodiments, the injectable BMP-2 is in lyophilized form, as described herein. The kit can comprise a plurality of doses of injectable BMP-2 or the kit further comprises a pump for administering the 10 µg to about 1000 µg dosage of injectable BMP-2.

The aqueous carrier may comprise a buffering agent comprising tris(hydroxymethyl)aminomethane (Tris), ethylenediaminetetraacetic acid (EDTA), (2-[4-(2-hydroxyethyl)-1-piperazinyl]ethanesulfonic acid) (HEPES), sodium acetate, sodium citrate, sodium phosphate, 2-(N-morpholino)ethanesulfonic acid (MES), phosphate buffered saline (PBS), sodium phosphate, potassium phosphate, sodium chloride, potassium chloride, glycerol, calcium chloride, sucrose, glycine, L-glutamic acid, polysorbate 80 or a combination thereof.

In some embodiments, the kit further includes a package enclosing the components of the kit in a sterile condition. Such kits can further include a syringe or vial (e.g. terminally sterilized), and/or a transfer device such as a syringe, and/or a therapeutic substance. In some embodiments, the kit further comprises an implantable pump, as described above.

Having now generally described the invention, the same may be more readily understood through the following reference to the following examples, which are provided by way of illustration and are not intended to limit the present invention unless specified.

EXAMPLE

The experiments below suggest that a single injection of rhBMP-2 without a stationary matrix may be a viable and non-invasive treatment to augment fracture healing.

Figure 2:
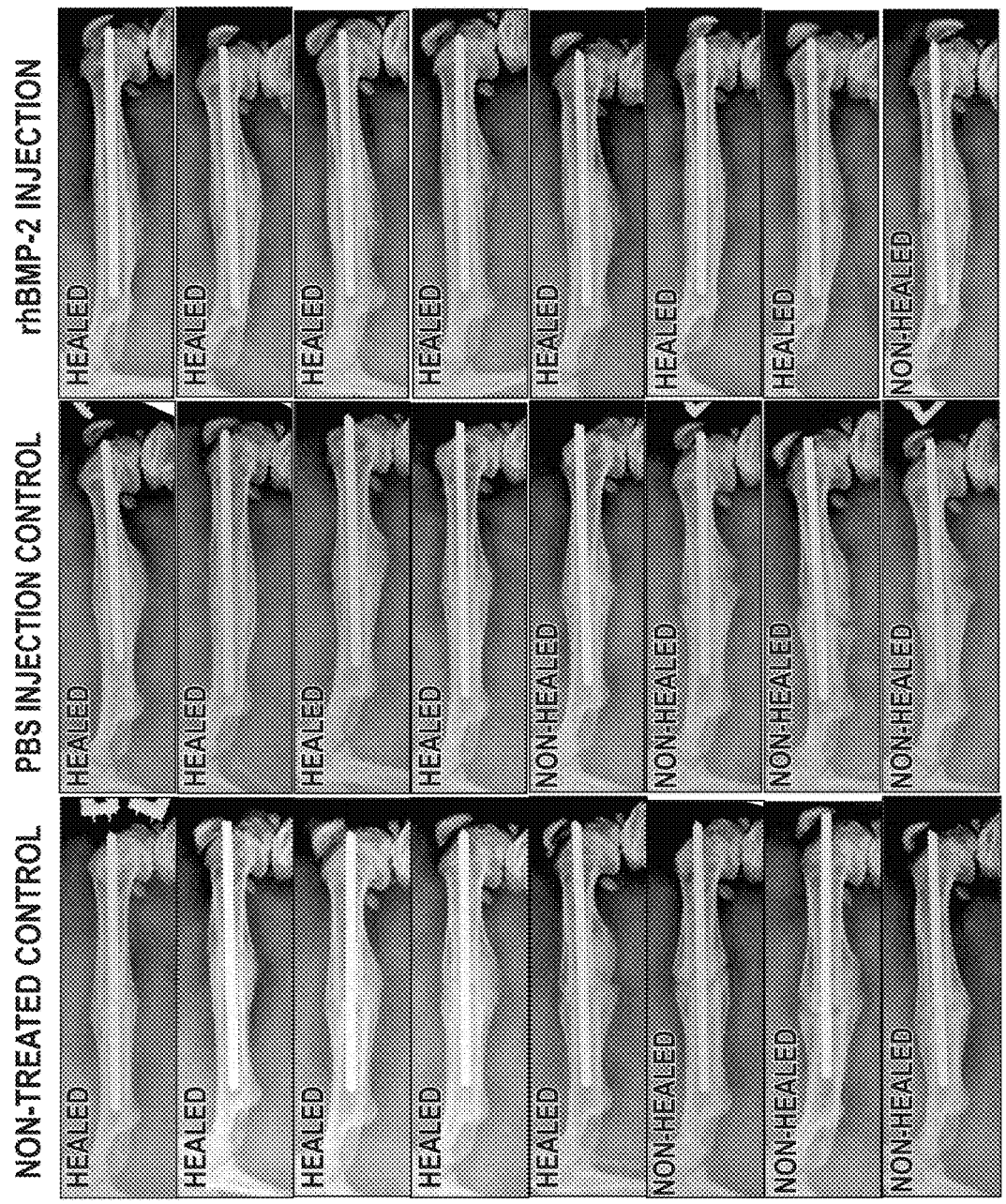
FIG. 2 illustrates radiographs taken four weeks post-surgery after a single injection of low-dose rhBMP-2 without a matrix, a non-treated control, or a PBS control was injected directly into an injury site in a rat. Twenty-four rats were broken into three groups of eight, where the long bones of the rats were directly administered either the single injection of low-dose rhBMP-2 without a matrix, the non-treated control, or the PBS control. Four weeks post-surgery, fracture healing was assessed using x-ray radiographs by three assessors blinded of the treatment groups. Bone strength was quantified using a three-point bending test of the fractured femur compared to a contralateral non-fractured femur.
Figure 4:
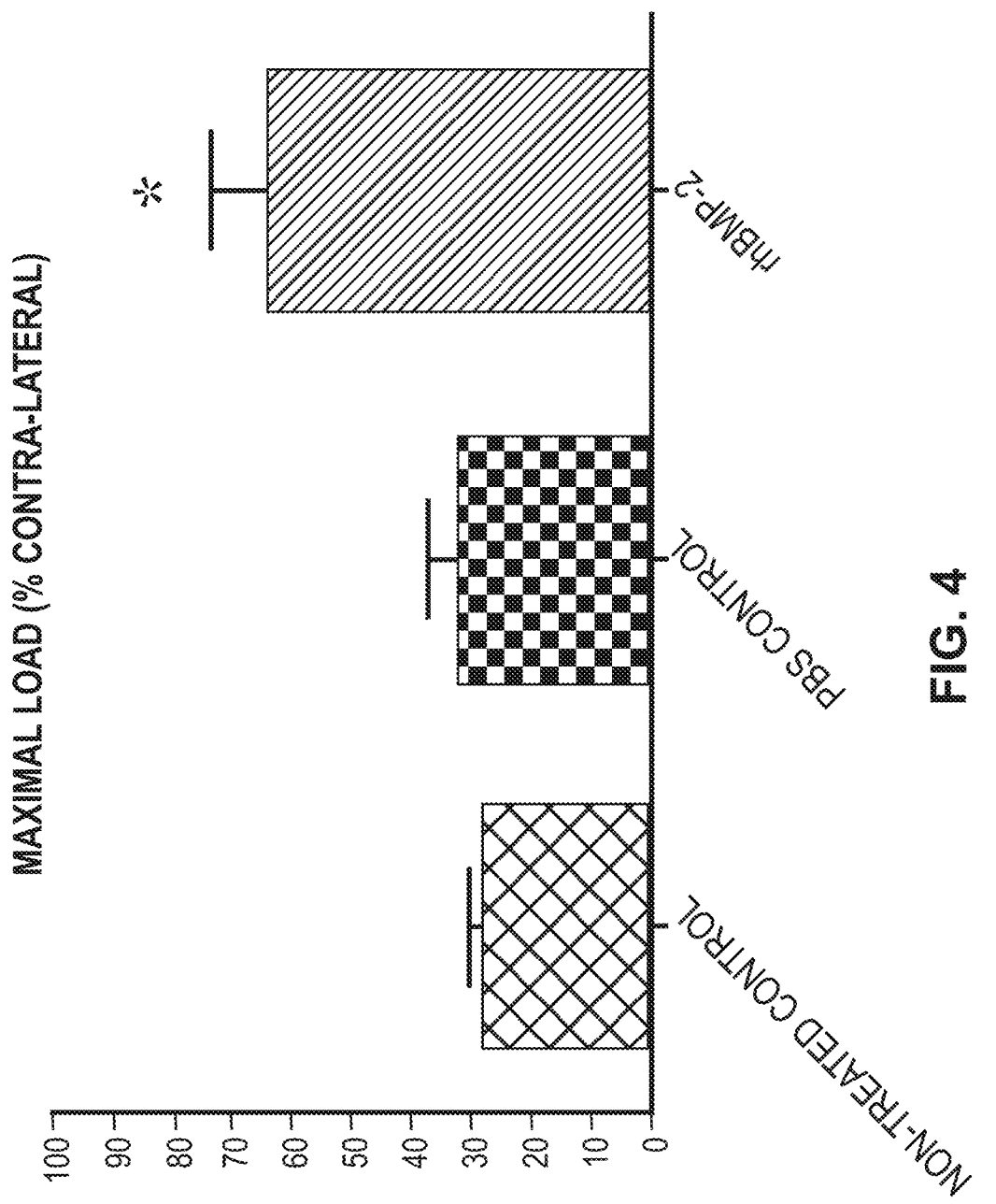
FIG. 4 is a graph depicting the maximal load percentage of the fractured femurs treated with the single injection of low-dose rhBMP-2 without a matrix, the non-treated control, and the PBS control compared to a contralateral non-fractured femur. Results of the graph were factored into bone strength using the three-point bending test.
Figure 5:
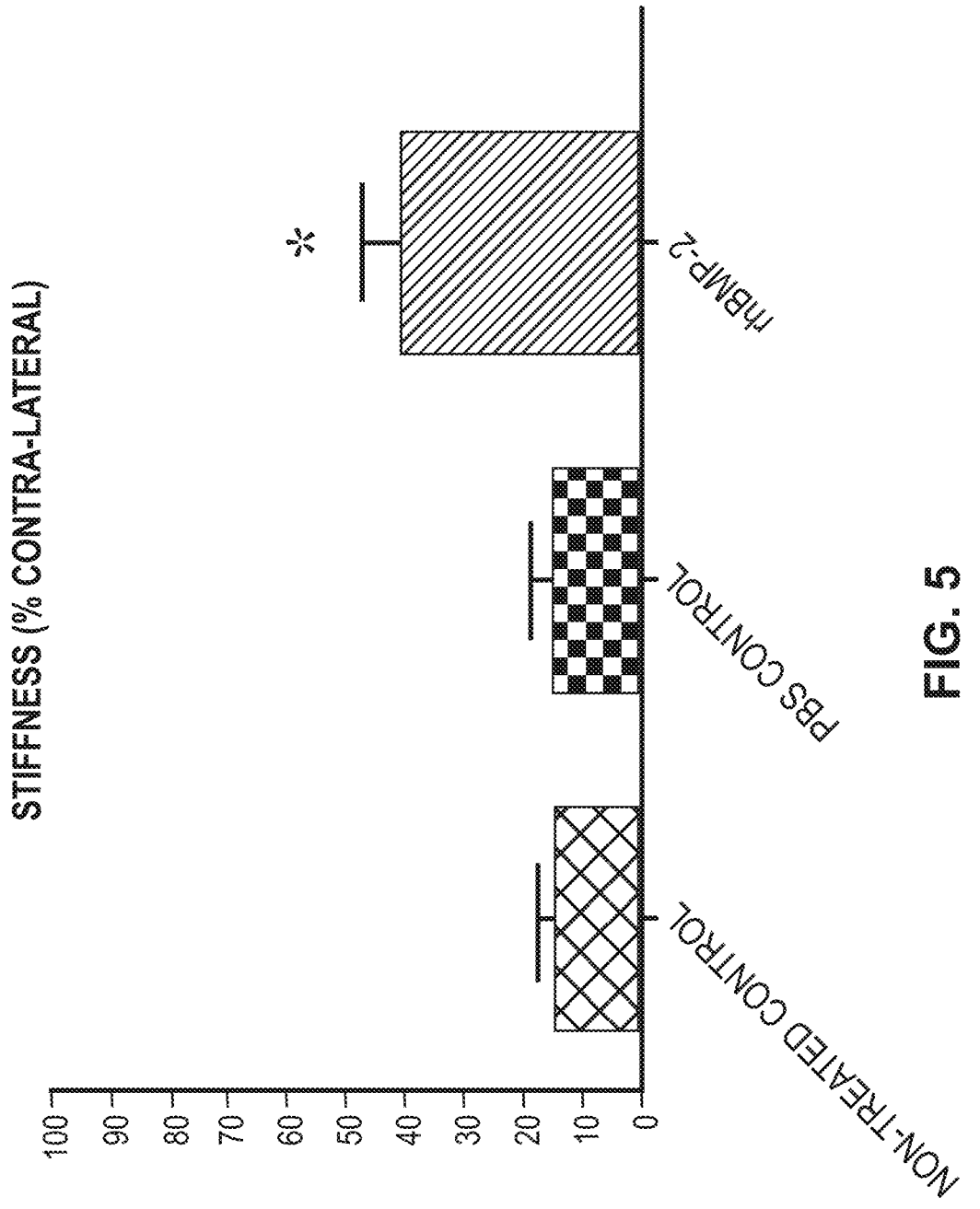
FIG. 5 is a graph depicting the stiffness percentage of the fractured femurs treated with the single injection of low-dose rhBMP-2 without a matrix, the non-treated control, and the PBS control compared to a contralateral non-fractured femur. Results of the graph were factored into bone strength using the three-point bending test.

Methods:

A rat fracture model was used to test the concept of a single injection of low-dose rhBMP-2 directly into the injury site without matrices (e.g., a stationary matrix, such as a collagen matrix). A unilateral fracture was created in the rat femur and stabilized with an intramedullary pin. A total of 24 rats were randomly assigned to receive either rhBMP-2, phosphate buffered saline (PBS) injection control or non-treated control (N=8/group). rhBMP-2 was dissolved in sterile water for injection to a final concentration of 0.28 mg/mL. A volume of 100 uL of either rhBMP-2 (a total of 28 ug) or PBS was injected directly into the injury site through a 21 gauge needle. After 4 weeks post surgery, fracture healing was assessed using x-ray radiographs by three assessors blinded of the treatment groups (FIG. 2). Bone strength was quantified using a 3-point bending test of the fractured femur compared to a contralateral non-fractured femur (FIGS. 4 and 5).

Results:

Radiographic fracture healing was defined as bridging of the cortical bone on the x-ray (FIG. 2). The group that was administered rhBMP-2 showed that seven rats healed, one rat did not heal, and there was an 88% healing. The group that was administered the non-treated control showed that 5 rats healed, 3 rats did not heal, and there was a 63% of healing. The group that was administered the PBS injection control showed that 4 rats healed, 4 rats did not heal, and there was a 50% of healing. More healed fractured were found in the rhBMP-2 group compared to the PBS or the non-treated control (FIG. 3). The mechanical strength of rhBMP-2 group was significantly ($p<0.05$) higher than that of the PBS injection or the non-treated control. FIG. 4 shows the maximal load percentage of the fractured femurs compared to a contralateral non-fractured femur. The rhBMP-2 performed better than both the PBS injection and the non-treated control. FIG. 5 shows the stiffness percentage of the fractured femurs compared to a contralateral non-fractured femur. The rhBMP-2 again performed better than the PBS injection and the non-treated control.

CONCLUSION

The data suggested that a single injection of rhBMP-2 without a stationary matrix may be a viable and non-invasive treatment to augment fracture healing. These results were surprising since the rhBMP-2 was not administered on a matrix and since the dose of the rhBMP-2 was low. In some embodiments, a dose as low as 0.28 mg/mL can be administered as the starting dose for human use.

It should be understood that the forgoing relates to exemplary embodiments of the disclosure and that modifications may be made without departing from the spirit and scope of the disclosure as set forth in the following claims.

What is claimed is:

1. A method of treating a bone defect, the method comprising administering to the bone defect an injectable solution comprising 28 µg of bone morphogenetic protein-2 (BMP-2) in an aqueous carrier, wherein the injectable solution has a pH of about 6.0, and wherein the injectable solution is administered as a single dose injection to the bone defect.

2. The method of claim 1, wherein the BMP-2 is recombinant human BMP-2 (rhBMP-2).

3. The method of claim 1, wherein the aqueous carrier comprises saline, dextrose, sterile water for injection, phosphate buffered saline, blood, or a combination thereof.

4. The method of claim 1, wherein the injectable solution further comprises a buffering agent comprising tris(hydroxymethyl)aminomethane (Tris), ethylenediaminetetraacetic acid (EDTA), 2-[4-(2-hydroxyethyl)-1-piperazinyl]ethanesulfonic acid (HEPES), 2-(N-morpholino)

ethanesulfonic acid (MES), sodium acetate, sodium citrate, sodium phosphate, potassium phosphate, phosphate buffered saline (PBS), sodium chloride, potassium chloride, calcium chloride, glycerol, sucrose, glycine, L-glutamic acid, polysorbate 80 or a combination thereof.

5. The method of claim 4, wherein the buffering agent comprises sucrose, glycine, L-glutamic acid, sodium chloride, polysorbate 80 or a combination thereof.

6. The method of claim 4, wherein the buffering agent in the injectable solution is at a concentration from about 1 mM to 100 mM.

7. The method of claim 1, wherein the injectable solution further comprises a clotting factor in an amount of about 0.0001% to about 5% of the injectable solution.

8. The method of claim 1, wherein (i) the injectable solution is administered percutaneously to a long bone fracture; or (ii) the injectable solution is injected directly into a fracture site that has a hematoma.

9. The method of claim 1, wherein the aqueous carrier is not osteoinductive or osteoconductive.

* * * * *